(12) United States Patent
Rajeswaran et al.

(10) Patent No.: US 7,508,500 B2
(45) Date of Patent: Mar. 24, 2009

(54) CHARACTERIZING ORGANIC MATERIALS IN A THIN FILM

(75) Inventors: Manju Rajeswaran, Fairport, NY (US); Thomas N. Blanton, Rochester, NY (US); Barbara J. Stwertka, Rochester, NY (US); Joseph L. Lippert, Rochester, NY (US); Christopher T. Brown, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 639 days.

(21) Appl. No.: 10/974,584

(22) Filed: Oct. 27, 2004

(65) Prior Publication Data

US 2006/0100793 A1    May 11, 2006

(51) Int. Cl.
G01N 21/35 (2006.01)
G01N 21/65 (2006.01)
G01N 23/20 (2006.01)

(52) U.S. Cl. ............... 356/72; 250/341.1; 356/301; 378/71

(58) Field of Classification Search ......... 356/301, 356/72
See application file for complete search history.

(56) References Cited

U.S. PATENT DOCUMENTS 6,858,454 B1 * 2/2005 Kanzawa et al. ......... 438/16
6,939,515 B2 * 9/2005 Carlson et al. .......... 422/101
7,234,365 B2 * 6/2007 Carlson et al. ........... 73/866
7,329,592 B2 * 2/2008 Myerson et al. ......... 438/497
2007/0254141 A1 * 11/2007 Morse et al. ............ 428/220

FOREIGN PATENT DOCUMENTS

GB    2 084 580    4/1982

OTHER PUBLICATIONS

H. Takahashi, et al., Bull. Chem. Soc., Japan, "Quantitative Analysis of Mixtures of L-Glutamic Acid Polymorphs by X-Ray Diffraction", vol. 35, 1962, pp. 923-926.
D. H. Doff, et al., "Determination of α-Impurities in the β-Polymorph of Inosine Using Infrared Spectroscopy and X-ray Powder Diffraction", 1986, vol. III, pp. 179-182.
A. Ennaoui, et al., Journal of Materials Science Letters, "Infrared Spectroscopic and X-ray Diffraction Characterization of Iron Disulphide Thin Films Prepared by Metal-Organic Chemical Vapour Deposition", 1992, vol. 11, pp. 1131-1133.
J. Bernstein, J. Phys. D: Appl. Phys., "Crystal Growth, Polymorphism and Structure-Property Relationships in Organic Crystals", 1993, vol. 26, pp. 866-976.

(Continued)

*Primary Examiner*—F. L Evans
(74) *Attorney, Agent, or Firm*—Arthur E. Kluegel; Raymond L. Owens

(57) ABSTRACT

A process for characterizing the phase of an organic material in a thin film comprises employing a reference spectrum library for potential phases, subjecting the film to a vibrational spectroscopy measurement to obtain a resulting spectrum; and comparing the resulting spectrum to those in the reference library to characterize the phase of the organic material.

35 Claims, 12 Drawing Sheets

OTHER PUBLICATIONS

Thin Films Science and Technology, 7—"Thin films by Chemical Vapour Deposition" by C.E. Morosanu, Elseview, Amsterdam-Oxford—New York- Tokyo—1990 (Book).
Thin Film Materials, Stress, Defect Formation and Surface Evolution, L.B. Freund,S. Suresh, Cambridge University Press, Publishedby the Press Syndicate of the University of Cambridge, First published 2003 (Book).
Thin Film Device Applications, Kasturi Lal Chopra and Inderjeet Kaue, Indian Institute of Technology, Newe Delhi, India, Plenum Press, NewYork and London (Book) 1983.

* cited by examiner

CHARACTERIZING ORGANIC MATERIALS IN A THIN FILM

FIELD OF THE INVENTION

This invention relates to processes for characterizing the phase and composition of organic materials in a thin film or a thin-film containing device.

BACKGROUND OF THE INVENTION

Most organic materials coated or deposited in thin films are, at some stage in their manufacture, crystalline compounds. Crystalline materials can exhibit a phenomenon referred to as "polymorphism," the ability of a substance to crystallize in more than one crystal structure formation. Over a quarter million such examples have been reported in the literature (J. Bernstein, *J. Phys. D: Appl. Phys.,* 26, B66-B76, 1993). Each modification or "polymorph" has the same chemical structure, but differs in the packing of molecules within the crystal lattice. These different polymorphs can have profoundly different physical or electronic properties, including color, optical properties, melting point, reactivity, solubility, density, and toxicity (T. L. Threlfall, *Analyst,* 120, 2435-2460, 1995). While most of the literature relating to polymorphs has focused on pharmaceutical products (S. R. Byrn, *Solid State Chemistry of Drugs,* Academic Press, New York, 1982), it is equally important in the design or manufacture of thin films and thin film-containing devices to be able to accurately characterize both the incorporated state or phase of such organic materials as well as the presence or absence of other organic species. Unfortunately, the processes by which such films are created can often alter or determine the final phase of the organic materials in the thin films, and so it is very desirable to identify a process by which the phase of these organic materials in such thin films or thin film-containing devices can be characterized.

The presence or absence of many organic materials in a thin film or thin film-containing device may be determined by conventional analytical techniques, such as high performance liquid chromatography or, for polymorphic phases in particular, hot stage microscopy (W. C. McCrone in *Physics and Chemistry of the Organic Solid State,* D. Fox, M. M. Labes and A. Weissberger, eds, Interscience, New York, 1965, vol. II, p. 725). But such techniques require destructive sample preparation, which can be both time-consuming and unsuitable for a manufacturing environment. Further, the sample preparation process can alter or obscure the phase of the organic materials of interest.

The most commonly used technique for identifying and distinguishing polymorphic materials is X-ray diffraction (XRD) (H. Takahashi, T. Takenishi and N. Nagashima, *Bull. Chem. Soc. Japan,* 35, 923, 1962). An XRD single crystal structure determination, although potentially time-consuming, can reveal the precise molecular structure and unique crystal habitat of the material. However, XRD single crystal determination is not suitable for use in thin films as it requires a single crystal oriented in the X-ray beam, not an array of randomly oriented crystals as may be found in a film. The more easily attainable XRD powder pattern, obtained from a randomly-arrayed mass of crystals, does not generally provide direct structural information, but its characteristic pattern of diffraction intensity as a function of diffraction angle (the two-theta angle, measured in degrees) can provide a multiplicity of peaks that taken in combination can uniquely and unequivocally distinguish one polymorphic form from others. Unfortunately, when coated as or in a thin film, many polymorphs can appear to be amorphous in nature, that is, failing to show the XRD diffraction pattern expected for a crystalline material. This occurs because some polymorphic materials in the thin films lack the long-range order of isolated crystals that is detectable by XRD, though they maintain a short-range order, which determines their polymorphic character.

Even for those materials that may exhibit a diffraction pattern as or in a thin film, an additional problem may occur when these films are part of a thin film-coated device. These devices, such as an organic electroluminescent (EL) device (C. H. Chen, J. Shi and C. W. Tang, *Macromol. Symp.* 125, 1-48, 1997), typically are constructed with multiple layers, one or more of which may attenuate or be impermeable to X-rays, thus making the characterization of polymorphs in a thin film incorporated as part of such a device extremely difficult or impossible by the XRD technique alone.

Vibrational spectroscopy, in particular Raman spectroscopy or infrared (IR) spectroscopy (N. B. Colthup, L. H. Daly and S. E. Wiberley, *Introduction to Infrared and Raman Spectroscopy,* Academic Press, New York, $2^{nd}$ ed. 1975) can be used to distinguish one polymorphic material from another in a thin film (though commonly this has been limited to thin films between salt or KBr plates, see M. Kuhnert-Brandstatter and E. Junger, *Spectrochim Acta, Part A,* 23, 1453, 1976) or in a thin film-device but only if the polymorph has been previously characterized. Vibrational spectroscopy can detect the short-range order of a polymorph in a thin film, but cannot in itself fully characterize the molecular structure or crystal habit of the material.

Doff, et. al. have compared separately the utility of X-ray diffraction and infrared spectroscopy in quantitative determination of the polymorphs of alpha and beta inosine, but these measurements were not in a thin film or thin film-device and required extensive sample preparation and manipulation (D. H. Doff, F. L. Brownen and O. I. Corrigan, *Analyst,* 111, 179-182, 1986). In the preparation of a desired crystalline form of the drug ranitidine, Crookes used separately the infrared spectrum of an oil mull preparation of the drug and an X-ray powder diffraction of the drug to identify the desired form for patent claims (D. L. Crookes, GB 2084580A, Apr. 15, 1982).

Another technique, microfluorescence can be used to distinguish previously characterized polymorphs in a thin film, but only if the materials of interest exhibit a fluorescence spectrum and that spectrum is sufficiently distinct from the fluorescence spectra of other materials in the thin film or thin film-device. A further technique, ellipsometry, which uses polarized light to probe the dielectric properties of thin films can exhibit a sensitivity to optical absorption which can interfere with measurements and may require a detailed knowledge of the real and imaginary parts of the substrate refractive index which may not be available. For some problems, such as the dopants used in small quantities in the thin films of organic electroluminescent (EL) devices, ellipsometry may be insufficiently quantitative.

It is a problem to be solved to provide a non-destructive process for characterizing the polymorphic character or phase of an organic material as a thin film or incorporated in a thin film as well as the presence or absence of other organic materials. It is a further problem to be solved to characterize such phases when the thin film is shielded by an X-ray attenuating medium as when the thin film is incorporated into an electronic device, such as an organic electroluminescent (EL) device. It is a further problem to be solved to be able to quantify the absolute or relative amounts or coverage of such phases in a thin film or a thin film-containing device. Additionally, it is a problem to be solved to determine the thickness of a thin film of an organic material. It is a further problem to be solved to make these determinations of phase, amounts, and film thickness by a non-destructive technique applicable in a manufacturing environment.

SUMMARY OF THE INVENTION

This invention provides a process for characterizing the phase of an organic material in a thin film comprising:

establishing a reference spectrum library for potential phases;

subjecting the film to a vibrational spectroscopy measurement to obtain a resulting spectrum; and comparing the resulting spectrum to those in the reference library to characterize the phase of the organic material.

In another embodiment, the invention encompasses a process for identifying a known phase, an undesirable phase or impurity, or of detecting the presence of an unknown phase of an organic material in a thin film, comprising:

establishing a reference spectrum library for known phases;

subjecting the film to a vibrational spectroscopy measurement to obtain a resulting spectrum; and comparing the resulting spectrum to those in the reference library to ascertain the identity of the known phase, the undesirable phase or impurity, or the presence of an unknown phase.

It also embodies a process for characterizing the phase of an organic material in a thin film comprising:

establishing a reference library containing the X-ray powder diffraction patterns for potential phases;

subjecting the thin film to an X-ray diffraction measurement to obtain a resulting pattern;

comparing the resulting pattern to those in the reference library to characterize the phase of the material in the thin film.

A further embodiment is the process for determining the relative amounts of two or more phases of an organic material in a thin film comprising:

establishing for each phase and mixture of phases of interest a quantitative calibration curve relating selected peak heights or peak areas of that phase as determined by vibrational spectroscopy to the amount present;

subjecting the thin film to a vibrational spectroscopy measurement to obtain a resulting spectrum; and utilizing the calibration curves for each phase to compare the peak heights or peak areas for phases of interest to calculate the relative amounts of each phase.

Finally it embodies the process for determining the absolute amount of the phase of an organic material in a thin film of known thickness or the thickness of a known organic material comprising:

establishing for that phase a quantitative calibration curve relating selected peak heights or peak areas of that phase as determined by vibrational spectroscopy to the amount present or to the thickness of the known material;

subjecting the thin film to a vibrational spectroscopy measurement to obtain a resulting spectrum; and utilizing the calibration curve for the phase of interest to compare the peak heights or peak areas for phase of interest to calculate the absolute amount of that phase for the known film thickness or to calculate the thickness of the known material.

The process of the invention enables determinations of phase, amounts, and film thickness of organic materials by a non-destructive technique applicable in a manufacturing environment.

DETAILED DESCRIPTION OF THE INVENTION

Figure 1:
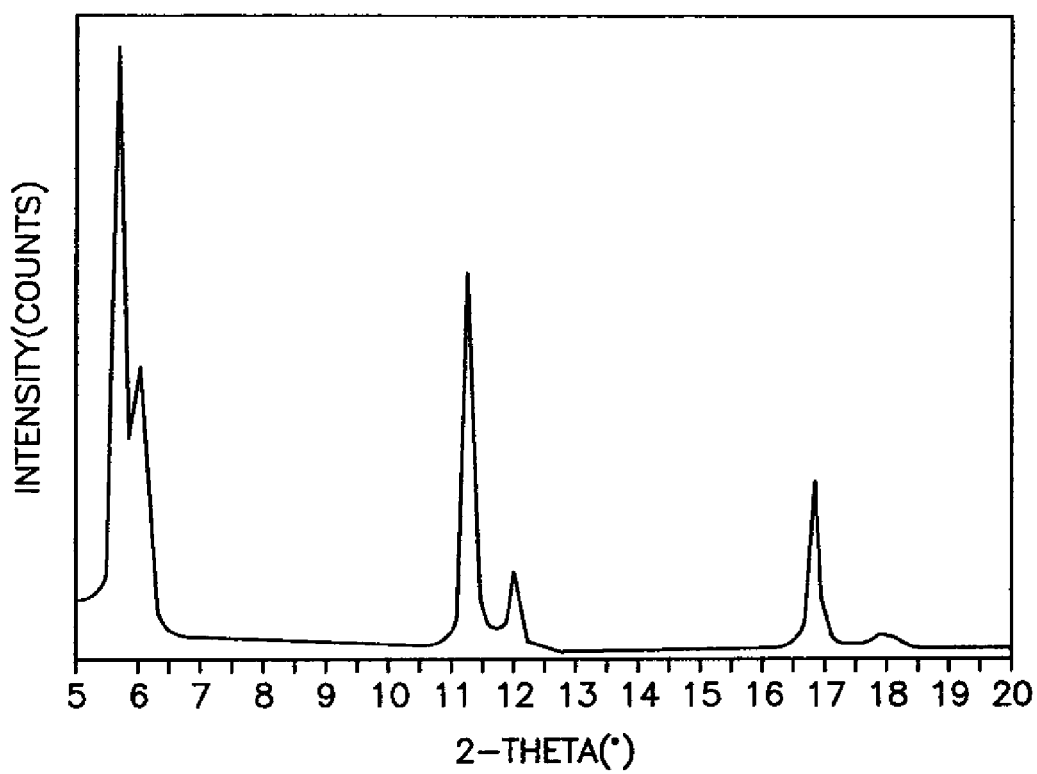
FIG. 1 shows the X-ray diffraction pattern of a crystalline 40 nm thin film of pentacene deposited on 20 nm gold on glass. 1.54 nm and 1.44 nm pentacene polymorphs are detected.

As described in the Background of the Invention, the most definitive method for characterizing the polymorphs of a crystalline material is by single crystal X-ray diffraction, a technique that can reveal the precise molecular structure and unique crystal habitat of the material. However, this powerful technique requires that a single crystal be precisely aligned in an X-ray beam, that large amounts of diffraction data be collected, and that the data be manipulated by computer techniques to elucidate the crystal structure. It is not possible to perform such procedures either on randomly ordered crystals as would be found in a thin film or thin film-containing device.

Once single crystal X-ray diffraction has characterized a particular polymorph, however, a unique and distinguishing X-ray powder diffraction (XRPD) spectrum can quickly and easily be obtained by placing a randomly-oriented sample of the crystals in an X-ray beam and measuring the diffraction intensity of the beam as a function of the diffraction angle (the so-called "two-theta angle", measured in degrees). While XRPD does not generally provide direct structural information, it does provide a multiplicity of diffraction peaks that taken in combination can uniquely and unequivocally distinguish one polymorphic form from others, especially when used in conjunction with elemental analysis or other analytical techniques that identify the forms as having the same molecular constituents. Unfortunately, when the organic crystalline materials are arrayed as a thin film or incorporated into a thin film, they may appear non-crystalline or amorphous to an X-ray beam because they lack long-range order while maintaining the short-range order of the polymorphic form. Further, it may not be possible to orient the film in such a way as to produce a useful XRPD spectrum.

Even for those materials that may exhibit a diffraction pattern as or in a thin film, an additional problem may occur when these films are part of a thin film-coated device. These devices, such as an organic electroluminescent (EL) device, typically are constructed with multiple layers, one or more of which may attenuate or be largely impermeable to X-rays, thus making the characterization of polymorphs in a thin film incorporated as part of such a device extremely difficult or impossible by XRD techniques alone.

Fortunately, vibrational spectroscopy techniques, which can detect short-range order, can be used to distinguish amongst different organic materials and their various polymorphic forms in thin films and can also be used in environments where X-rays would be attenuated. Vibrational spectroscopy can often function in environments where other techniques, such as fluorescence, could not be used because of interferences by materials other than those of interest. This is particularly useful for thin films that are part of electronic devices, such as organic electroluminescent (EL) devices. In its simplest form, an organic EL device is comprised of an anode for hole injection, a cathode for electron injection, and an organic medium sandwiched between these electrodes to support charge recombination that yields an emission of light. These devices are also commonly referred to as organic light-emitting diodes, or OLEDs, and often contain both X-ray attenuating materials and fluorescent compounds.

Vibrational spectroscopy is a technique well known in analytical chemistry (H. A. Willis, J. H. van der Maas, R. G. J. Miller, *Laboratory Methods in Vibrational Spectroscopy*, Wiley, Chichester, $3^{rd}$ ed., 1987). Briefly, it consists of directing a beam of electromagnetic energy towards a sample and measuring the amount of that energy that is absorbed or scattered by the sample as a function of the wavelength of the energy. In vibrational spectroscopy, the wavelength range of the directed energy is chosen so as to excite vibrational states of the molecules of interest, such as stretching or bending motions. While several modalities of vibrational spectroscopy have been described in the literature, the two of greatest utility in the present invention are infrared (IR) spectroscopy and Raman spectroscopy. In infrared spectroscopy, the characteristic spectrum is derived primarily from the absorption of the incident energy while in Raman spectroscopy the characteristic spectrum derives primarily from the scattering of energy. Infrared spectroscopy is often divided approximately into three ranges: the far infrared (200 to 10 $cm^{-1}$), the mid infrared (4,000 to 200 $cm^{-1}$) and the near infrared (12,500 to 4,000 $cm^{-1}$). For the purposes of this invention, both the far infrared and the mid infrared (commonly referred to simply as "infrared") have proved to be particularly useful, though recent advances have also improved the usefulness of near infrared (B. G. Osborne, T. Feam and P. H. Hindle, *Practical NIR Spectroscopy*, Longmans, Harlow, $2^{nd}$ ed. 1993). Also, in this invention, Raman spectroscopy has proved particularly useful. Modern analytical technologies, including lasers that emit high intensity monochromatic infrared energy (J. G. Grasselli and B. J. Bulkin, *Analytical Raman Spectroscopy*, Wiley, New York, 1991) and Fourier transform techniques (P. J. Hendra, C. Jones and J. Warner, *Fourier Transform Raman Spectroscopy*, Ellis Horwood, 1991), have in great degree helped to overcome some of the limitations of vibrational spectroscopy techniques, rendering them particularly suitable for use in the present invention. Both infrared and Raman spectroscopy may be enhanced with other technologies, such as microscopy (F. J. Bergin and H. F. Shurvell, *Appl. Spectrosc.*, 43, 516, 1989), to improve analytical performance.

In this invention, we "train" vibrational spectroscopy methods to recognize organic materials and their polymorphic forms using crystalline materials identified by X-ray diffraction and then utilize those vibrational spectroscopy methods to characterize those materials or determine their absence in a thin film or thin film device where the absence of long-range order would render X-ray diffraction impotent. To accomplish this, vibrational spectroscopy is used in this invention in conjunction with the X-ray diffraction spectra to establish a reference library of compounds and their polymorphs, each compound or polymorph characterized by the X-ray spectrum having a one to one correspondence with a vibrational spectroscopy measurement. Each polymorph of a given compound is likely to have several vibrational spectroscopy peaks that taken together uniquely distinguish it from another polymorph. To identify the polymorphs contained in a given thin film or thin film-containing device, in this invention the thin film or thin film-containing device is subjected to a vibrational spectroscopy analysis, and the observed peaks compared to the spectra in the reference library. If the peaks from the vibrational spectrum of the thin film or thin film-containing device match that of the reference library spectrum in frequency and relative intensity, then that polymorph is present. If the characteristic peaks for that polymorph are absent, then it can be concluded that the polymorph is not present or present in only small amounts. If, as is likely in some thin films or thin film-containing devices, the vibrational spectrum shows additional or possibly overlapping peaks to that of the reference spectrum, a selection of peaks from the spectrum in the reference library may be chosen to ascertain a match to a high degree of probability. Such matches may be made numerically, visually, or by use of a computer program.

Additionally, the process described in this invention can also be employed to determine relative or absolute amounts or coverage of the polymorphic phases identified in the reference library. To do so, "working" or calibration curves of selected peak heights or peak areas for each polymorphic phase and combination of phases are established by vibrational spectroscopy as a function of polymorph concentration. Then the thin film is subjected to a vibrational spectroscopy measurement. The ratios of the selected peak heights or peak areas of any two or more identified phases can be used with the calibration curves to determine relative amounts of the polymorphic phases. Additionally, if the thickness of the thin film is known, the absolute amount or coverage of any identified polymorphic phase can be determined. It may also be possible to determine the relative or absolute amounts or coverage despite the shielding by an X-ray attenuating medium. Such determinations may be made numerically, visually, or by use of a computer program.

The thickness of the films analyzed can range from 3 to 1000 nm or higher and typically from 5 to 500 nm.

Because this invention provides a way of pre-establishing a correspondence between time-consuming and elaborate X-ray diffraction techniques, which can fully characterize the polymorphic materials and a relatively simple vibrational spectroscopy measurement, it may also be easily adapted to a manufacturing environment where the use of X-ray diffraction might be impractical. This invention provides a way of conveniently monitoring the presence or absence of selected polymorphic phases in a thin film or thin film-containing device, such as organic EL devices, where the phase of the incorporated material may greatly affect ultimate film or device performance. Further, where calibration curves of the polymorphic phases have been established, this invention may provide a way of monitoring during manufacture the relative or absolute amounts or coverage of various phases in the thin film or thin film-containing device. In both cases, an automated system using technologies well-known in analytical chemistry may be adapted to use the processes of this invention.

EXPERIMENTAL

X-ray diffraction patterns of thin-films, single crystals, and powders were obtained with a Rigaku D2000 diffractometer, using a copper rotating anode X-ray source, Bragg-Brentano parafocusing diffractometer, diffracted beam monochromator tuned to CuKα radiation, and a scintillation detector. Experimental techniques used for data collection were generated by known methods such as described by F. Chung and D. Smith in *Industrial Applications of X-ray Diffraction*, Marcel Dekker Inc., New York, 2000.

Raman spectra of thin-film coatings, single crystals and powders were obtained with a JY-Horiba LabRam micro-Raman spectrometer, using either 633 nm or 785 nm excitation and 180 degree backscatter. The micro-Raman system has a spot analysis size of approximately 2 microns in diameter and approximately 8-10 microns in the film thickness direction (Z direction). For oriented single crystal measurements, a single crystal was glued on the end of an X-Ray mounting pin, and rotated under the micro-Raman to obtain spectra from the 3 distinguishable faces. Thin-film samples were typically prepared on Quartz substrates.

Infrared spectra of thin-film coatings on Si wafers were obtained on Digilab FTS 60 FT-IR (Fourier Transform-Infrared) spectrometers by either direct transmission through the wafer and coating (using an uncoated area of the wafer as a reference), or by single bounce Attenuated Total Reflectance (ATR) using a Ge element in a Harrick Seagull accessory. Some infrared spectra were also obtained by micro-transmission using a Nicolet micro-FT-IR spectrometer.

Infrared spectra for calibration curves were generated by the usual method (Griffiths, Peter R., de Haseth, James A., *Fourier Transform Infrared Spectrometry in Chemical Analysis*, Volume 83, John Wiley & Sons, 1986, chapter 10.) from coatings of known composition and thickness on Si wafers suitable for IR transmission.

Thin films of organic materials were suitably deposited through a vapor-phase method including sublimation, sputtering, chemical vapor deposition, or thermal transfer from a donor element. The material to be deposited by sublimation can be vaporized from a sublimation boat often comprised of a tantalum or graphite material. The substrate to be deposited on can be comprised of glass, metal, polymer, inorganic, or organic in composition, and can be a single crystal, polycrystalline, or amorphous.

Chemical Structures:

The molecular structure for organic chemicals used for organic thin film generation in the Examples and Comparative Examples are:

Structure 1

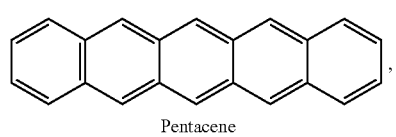

Pentacene

Structure 2

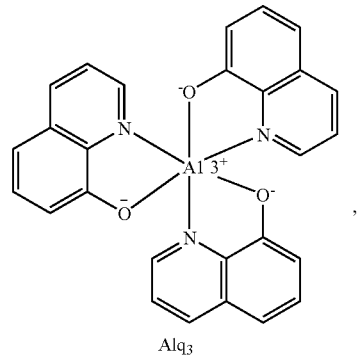

Alq$_3$

Structure 3

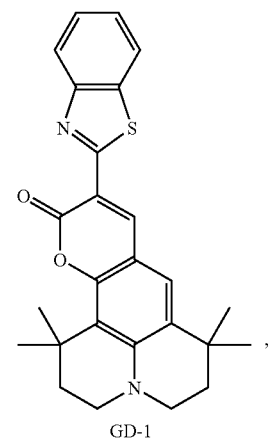

GD-1

Structure 4

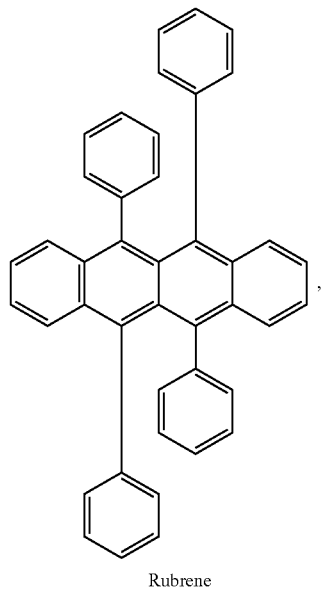

Rubrene

-continued

Structure 5

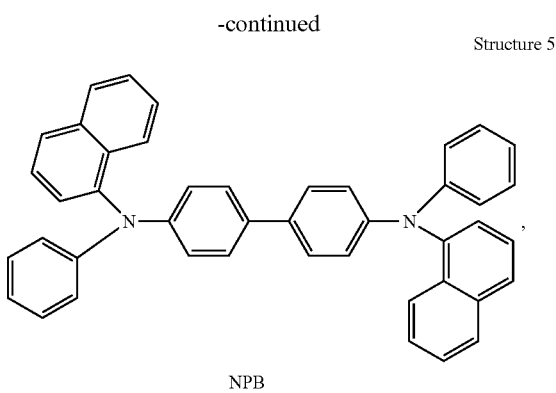

NPB

EXAMPLES

Comparative Example 1

Identification of the Phase of Pentacene in a Thin Film

The crystalline, organic material, pentacene (Structure 1), is often used in the fabrication of high-performance organic thin film transistors. Pentacene is known to exist in at least five polymorphic phases which may be designated as 1.41 nm, 1.45 nm, 1.50 nm, 1.54 nm, and 1.55 nm pentacene. Because these polymorphic phases have different physical properties, it is critical to know which phases are present in the thin film to be used as an organic thin film transistor. The XRPD patterns from powder samples for the five polymorphic phases are distinctly different and permit rapid identification of the polymorphic phase present in crystalline pentacene materials.

The diffraction pattern of a 40 nm thin film of pentacene deposited on a gold coated glass substrate is shown in FIG. 1. This diffraction pattern shows the presence of characteristic peaks that are attributed to the 1.54 nm and 1.44 nm phases of pentacene. Comparative Example 1 demonstrates that XRPD is capable of characterizing polymorphic forms of organic thins films if the films are crystalline.

Example 1

Invention: Identification of the Phase of $Alq_3$ in a Thin Film

Figure 2:
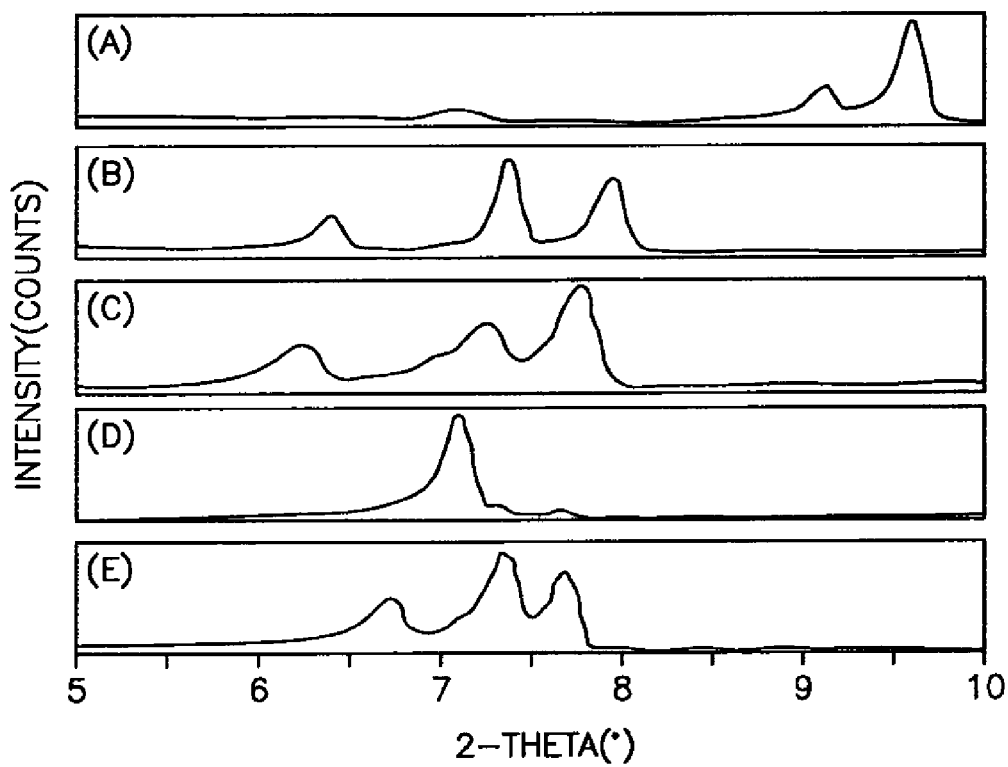
FIG. 2 shows X-ray powder diffraction patterns of five polymorphic forms of $Alq_3$ Aluminum trisoxine [alias, tris(8-quinolinolato)aluminum(III)], powder samples, (a) β, (b) α, (c) ε, (d) γ, and (e) δ.
Figure 3:
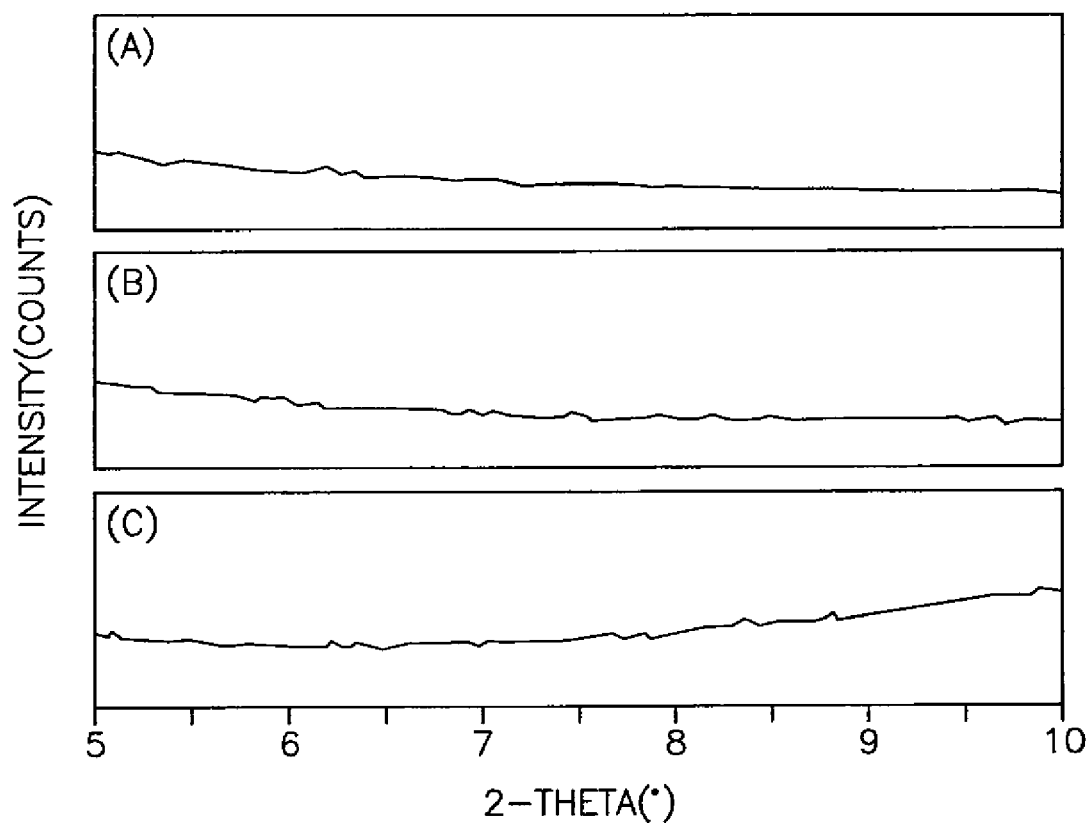
FIG. 3 shows X-ray powder diffraction patterns of amorphous thin film of $Alq_3$ deposited on glass (30, 100, and 1,000 nm, $Alq_3$ thickness).
Figure 4:
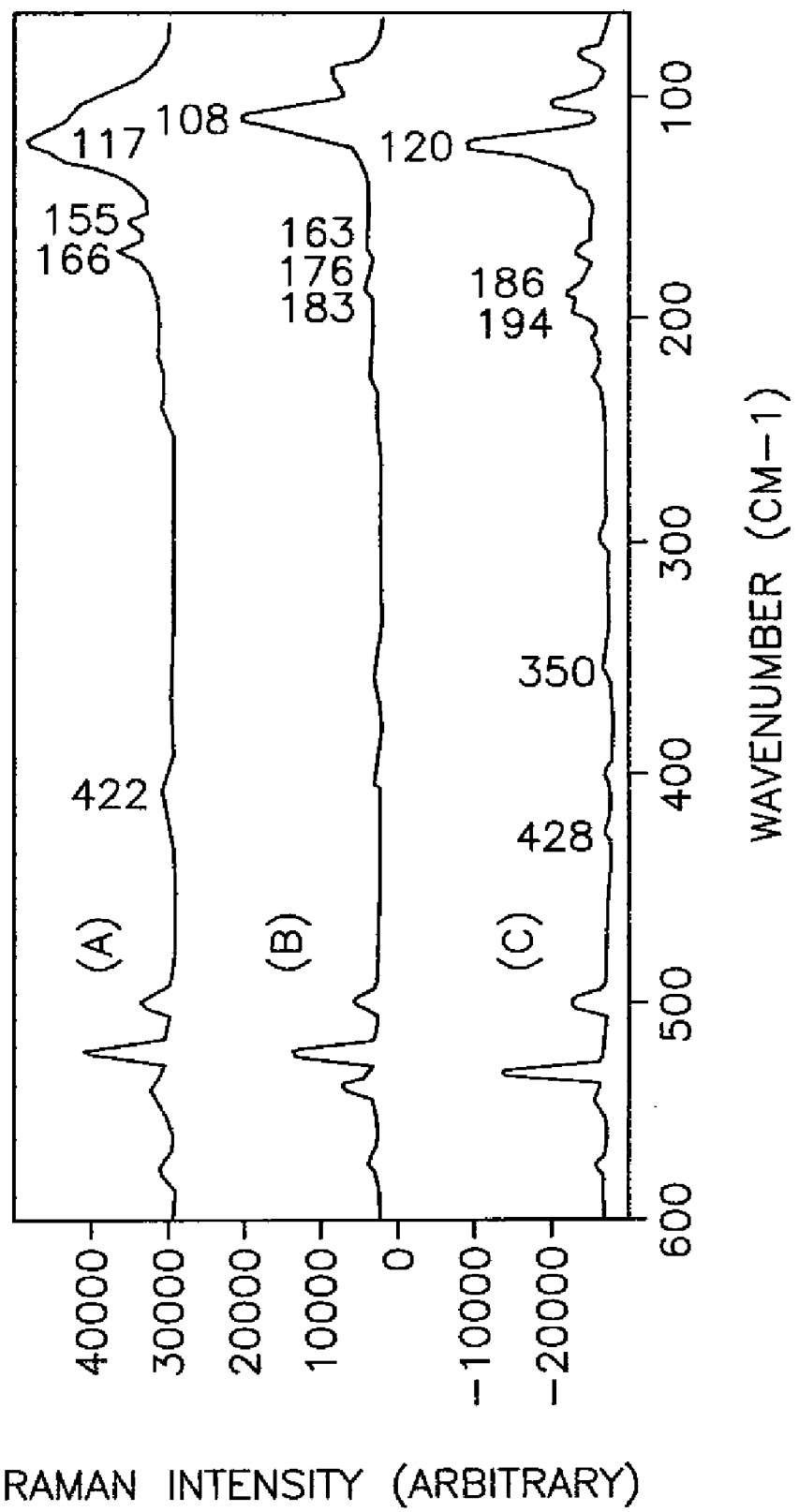
FIG. 4 shows overlays of micro-Raman spectra for crystalline powders for three polymorphs of $Alq_3$: (a) β, (b) α, and (c) δ.
Figure 5:
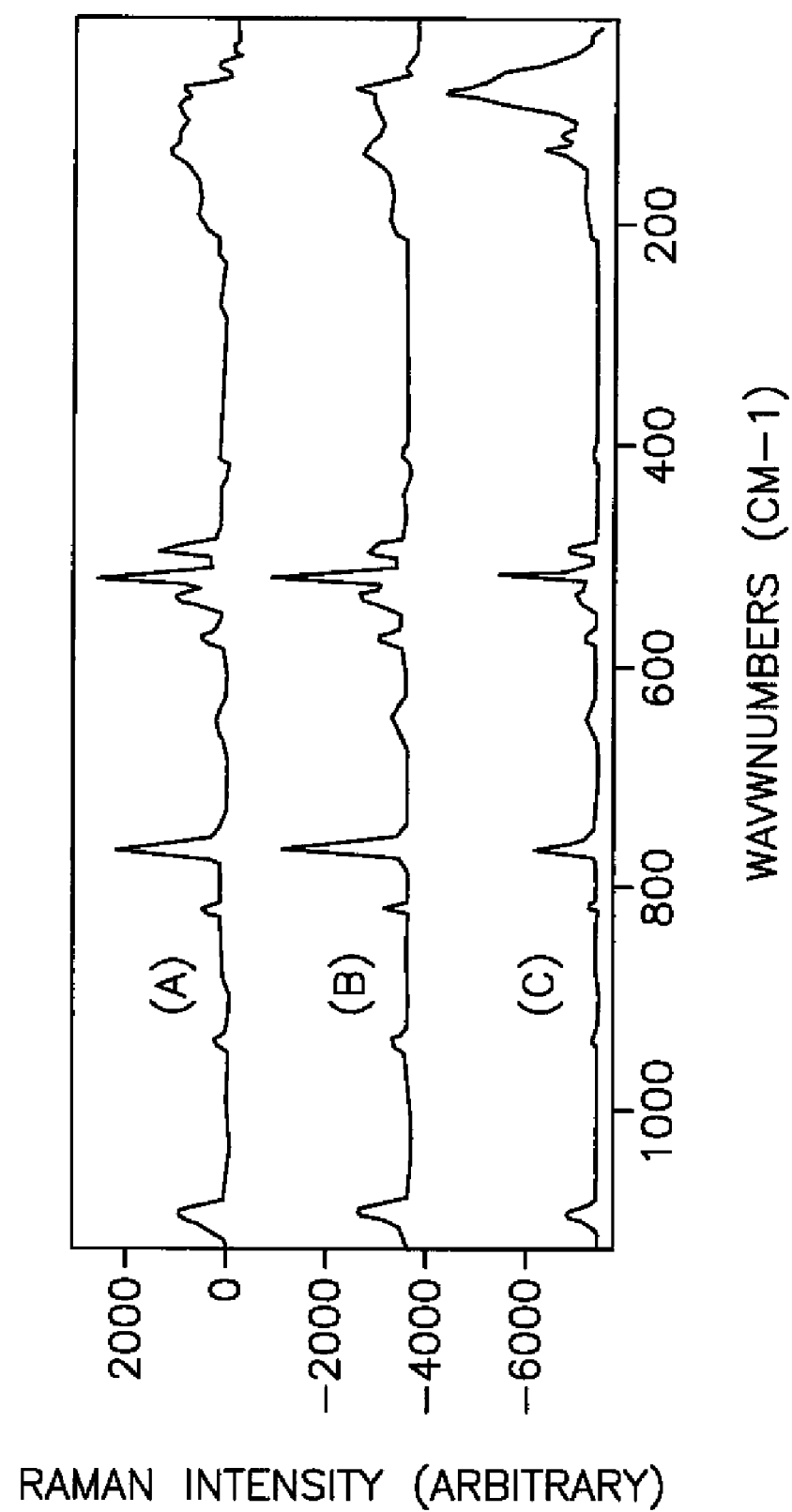
FIG. 5 shows Raman spectra from (a) 30 and (b) 100 nm thin films of $Alq_3$ deposited on glass, along with (c) the micro-Raman spectrum obtained from α-$Alq_3$ powder.

The crystalline, organic material, tris(8-hydroxyquinolinato) aluminum ($Alq_3$, Structure 2), is often employed as a thin film in a multilayer EL structure where it serves as part of the electron transport emitting layer. However, $Alq_3$ is known to exist in at least five polymorphic phases which may be designated as $\alpha$, $\beta$, $\gamma$, $\delta$, and $\epsilon$ $Alq_3$. Because these polymorphic phases have different physical properties, it is critical to know which phases are present in the thin film to be used as part of the EL device. The structural information for four polymorphic phases of $Alq_3$, $\alpha$, $\beta$, $\delta$, and $\epsilon$ has been obtained by single crystal XRD studies and the five polymorphs can be distinguished by X-ray powder diffraction (XRPD) measurements. The XRPD patterns from powder samples for the five polymorphic phases are distinctly different, as shown in FIG. 2 and permit rapid identification of the polymorphic phase present in crystalline $Alq_3$ materials. However, $Alq_3$ arrayed as a thin film coated on glass with thicknesses of 30, 100 or 1,000 nm failed to give a characteristic, identifiable XRPD pattern and instead appeared to be amorphous, as shown in FIG. 3, which prevented identification of the $Alq_3$ polymorph in any of the thin films. In the process of this invention, three of the polymorphic phases of $Alq_3$ were subjected to a micro-Raman analysis to give the Raman spectra overlaid as shown in FIG. 4. As can be seen from the overlaid spectra, the three polymorphic phases, of $Alq_3$ can be distinguished by a combination of unique scatter intensity peak positions and intensities. When a thin film of $Alq_3$ is created on a glass substrate the individual polymorphic phases can be distinguished through Raman analysis of the thin film by matching selected peaks in the thin film Raman spectrum to those in the micro-Raman analysis. In FIG. 5, the 30 and 100 nm amorphous thin films of $Alq_3$ from FIG. 3 are identified by Raman analysis as being the $\alpha$ polymorph, whereas XRPD was unable to identify the polymorphic form due to the amorphous character of $Alq_3$ in these thin films.

Example 1 demonstrates that XRPD is not capable of identifying polymorphic forms of organic thin films if the films are amorphous. Example 1 further demonstrates through this invention that by establishing a reference spectrum library of polymorphs of crystalline powders of an organic material by XRPD, subjecting these reference powders to a vibrational spectroscopy measurement such as Raman spectroscopy to establish a reference spectrum library, and subjecting an amorphous thin film of said organic material to a vibrational spectroscopy measurement to obtain a resulting spectrum, a comparison of the resulting spectrum to those spectra in the reference library can be used to characterize the polymorph of the amorphous material.

Example 2

Invention: Identification of the Phase of a Green Dopant in a Thin Film

Figure 6:
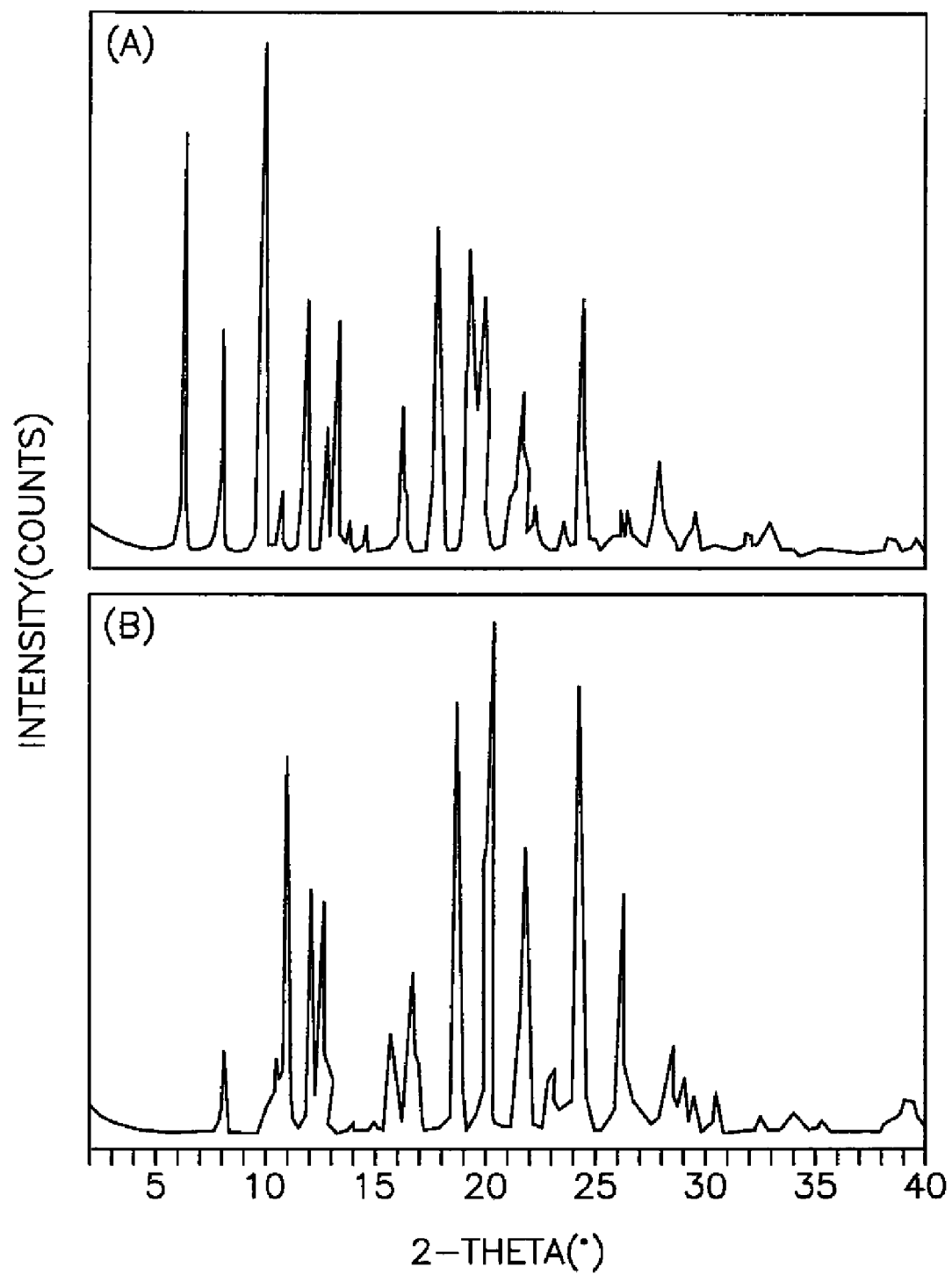
FIG. 6 shows X-ray powder diffraction patterns for crystalline powder samples of (a) Type I and (b) Type II GD-1
Figure 7:
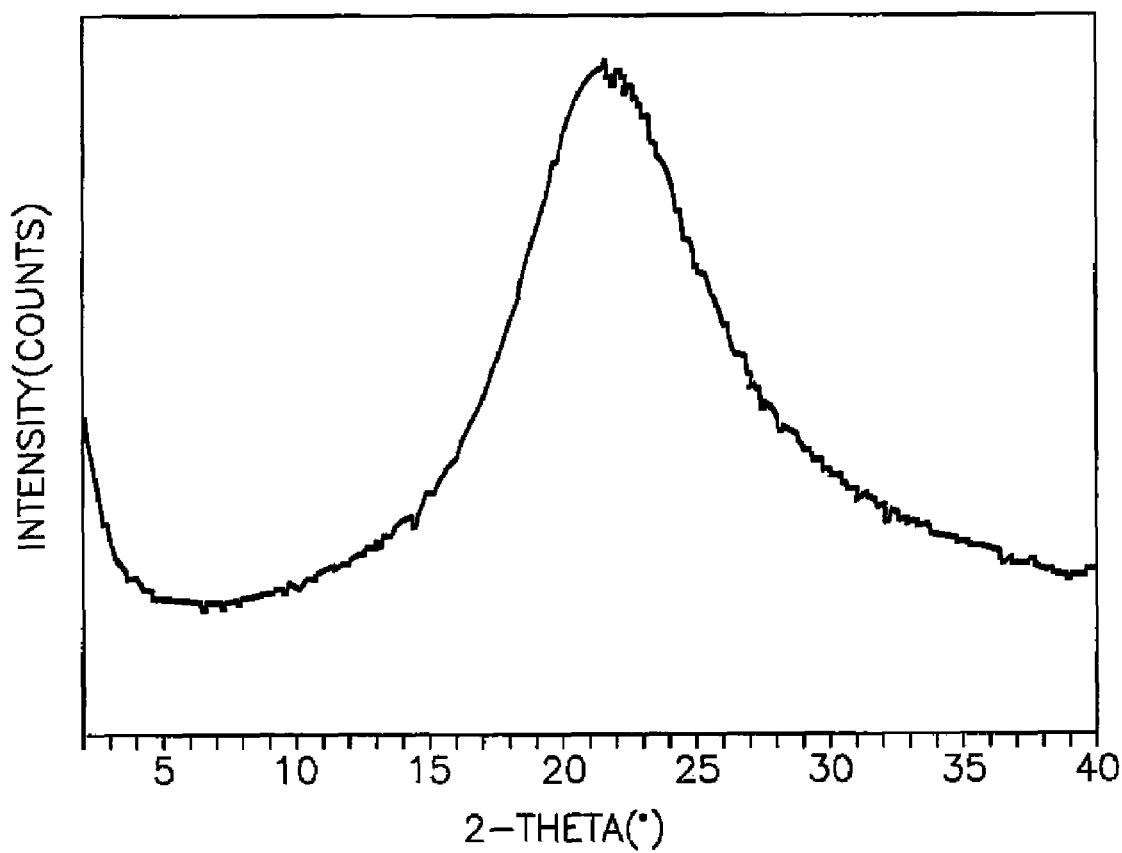
FIG. 7 shows an X-ray powder diffraction pattern of an amorphous film of GD-1 deposited on glass, 50 nm GD-1 thickness.
Figure 8:
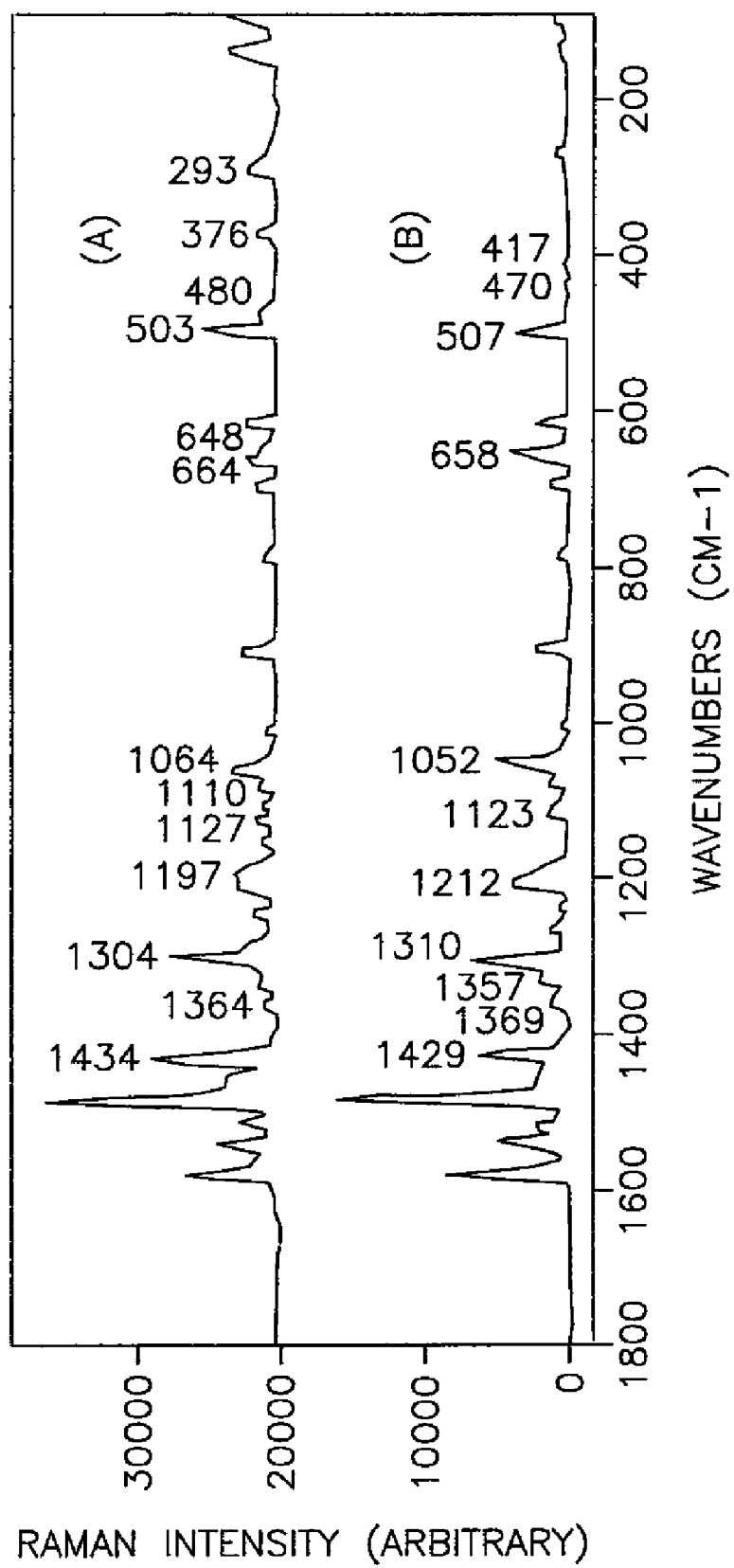
FIG. 8 shows Raman spectra of crystalline GD-1 powders—(a) Type I, (b) Type II. Unique bands for Type I and Type II are marked.
Figure 9:
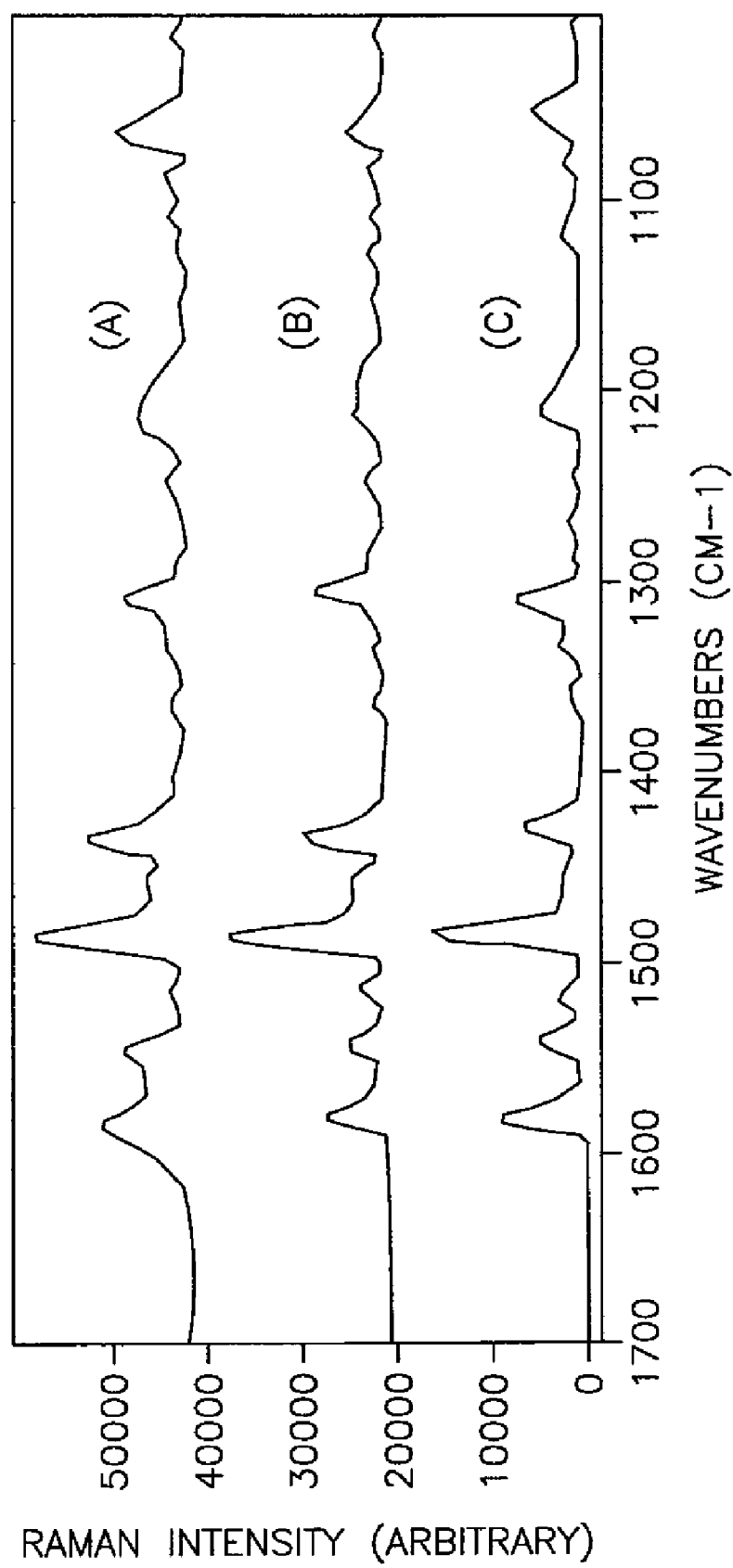
FIG. 9 shows an expanded view of region of interest of the Raman spectra of GD-1 (a) 50 nm GD-1 coated on glass with reference (b) Type I and (c) Type II spectra for comparison and identification of the polymorphic form in the amorphous film.

Dopants are organic fluorescent dye materials, which may be added, in small quantities to the emitting layers of an organic electroluminescent (EL) device in order to improve luminance efficiency and stability as well as adjust the color of the emitted light. It is critical for device functionality to be able to identify the phases of the dopant materials during the manufacture of a thin film of the EL device to maintain device functionality. GD-1 (Structure 3), a green dopant, which can be efficaciously added to a green-emitting layer, exists in at least two polymorphic phases. Though the two phases are not distinguishable by analytical techniques such as elemental analysis or HPLC, where they appear chemically identical, they can be easily distinguished by their X-ray powder diffraction patterns, as shown in FIG. 6, where the two phases are labeled Type I and Type II GD-1. When either phase of GD-1 is coated as a thin film, however, its powder diffraction pattern (FIG. 7) no longer shows the identifying peaks that permit distinguishing which phase is present in the film. As described in the process of this invention, however, the two phases identified by XRPD can be each correlated with their Raman spectra and unique peaks characteristic of each phase selected, as shown in FIG. 8, for establishing their entries in a reference library. When a thin film of GD-1 is subjected to a Raman spectroscopy measurement, the unique and identifying peaks found observed in the thin film sample can be correlated with those in the reference library Raman spectrum (FIG. 9) and the phases of GD-1 identified.

Example 2 demonstrates that XRPD is not capable of characterizing polymorphic forms of organic thin films if the films are amorphous. Example 2 further demonstrates through this invention that by establishing a reference spectrum library of polymorphs of crystalline powders of an organic material by XRPD, subjecting these reference powders to a vibrational spectroscopy measurement such as Raman spectroscopy to establish a reference spectrum library, and subjecting an amorphous thin film of said organic material to a vibrational spectroscopy measurement to obtain a resulting spectrum, a comparison of the resulting spectrum to those spectra in the reference library can be used to characterize the polymorph of the amorphous material.

Example 3

Invention: Determination of the Absolute Coverages and Thicknesses of $Alq_3$ and Rubrene in a Thin Film Using Data in the Reference Library Rubrene (Structure 4) is a yellow dopant, which may be added to $Alq_3$ in a thin film light-emitting layer of an EL device. For proper device functionality, it is critical to be able to monitor the relative ratio of Rubrene to an $Alq_3$ phase in the thin film. While such determinations can be done by destructive testing techniques, such as HPLC, these are time consuming and not suitable for an on-going manufacturing process. Ellipsometry may be insufficiently quantitative to provide an adequate determination while microfluorescence may suffer interference from fluorescing materials in the layer. By means of the process of this invention, utilizing a reference library of vibrational spectroscopy data, calibration curves and XRD data as needed, a rapid determination of the absolute coverages and thicknesses of Rubrene and $Alq_3$ phases in the thin film or thin film-containing device may be effected.

Thin films of Rubrene on IR transparent silicon and thin films of $Alq_3$ on IR transparent silicon were prepared for establishing calibration curves. Thin film thicknesses were defined using ellipsometry. These results are tabulated below in Table 1.

The infrared spectrum for the same film was collected and IR absorbances for the rubrene and $Alq_3$ bands previously calibrated are also shown in Table 2 along with the calculated coverages. The total calculated coverage from the IR calibration process as described in this example is also shown in Table 2 and is within 1% of the thickness as measured by ellipsometry. Furthermore the coverage ratio from the IR measurements (Table 2) is shown to be 71:29 rubrene:$Alq_3$, well within the experimental parameters of the coating process.

Example 3 demonstrates that the vibrational spectroscopy technique of IR is able to determine the absolute coverage of organic thin films. Example 3 further demonstrates through this invention that by establishing a reference spectrum library of polymorphs of crystalline powders of an organic material by XRPD, subjecting these reference powders to a vibrational spectroscopy measurement such as Infrared spectroscopy to establish a reference spectrum library, and subjecting a thin film of said organic material to a vibrational spectroscopy measurement to obtain a resulting spectrum, a comparison of the resulting spectrum to those spectra in the reference library can be used to determine absolute coverages and thicknesses of organic thin films.

Example 4

Invention: Determination of the Coverage of $Alq_3$ in a Thin Film on Silica Using Raman Spectroscopy Data in the Reference Library and Extension of the Example to Obtain Relative Coverage of Two Thin Film Materials Thin films of $Alq_3$ on fused quartz glass were prepared for establishing calibration curves. Thin film thicknesses were

TABLE 1

Film thickness calibration curve data

| Rubrene | | | | $Alq_3$ | | | |
|---|---|---|---|---|---|---|---|
| Nominal Thickness | Ellipsometry Thickness | Infrared Absorbance | Calculated Thickness | Nominal Thickness | Ellipsometry Thickness | Infrared Absorbance | Calculated Thickness |
| 80 nm | 88 nm | 0.0133 | 87 nm | 80 nm | 76 nm | 0.0326 | 74 nm |
| 160 nm | 175 nm | 0.0268 | 175 nm | 160 nm | 154 nm | 0.0685 | 155 nm |

Figure 10:
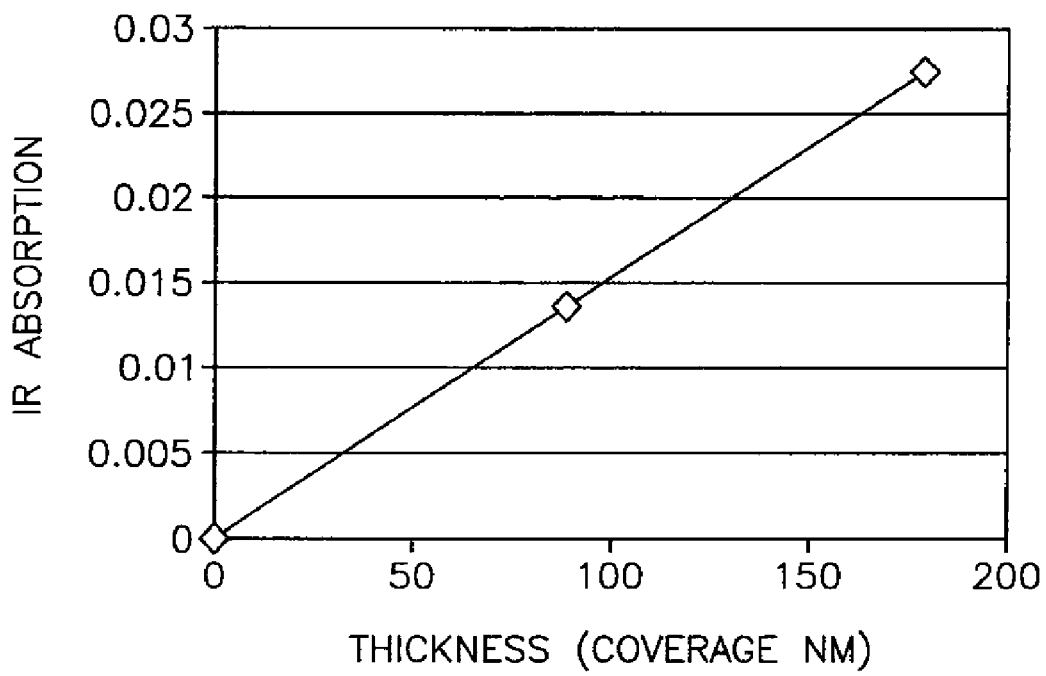
FIG. 10 shows a plot of IR absorbance as a function of rubrene thickness (coverage).
Figure 11:
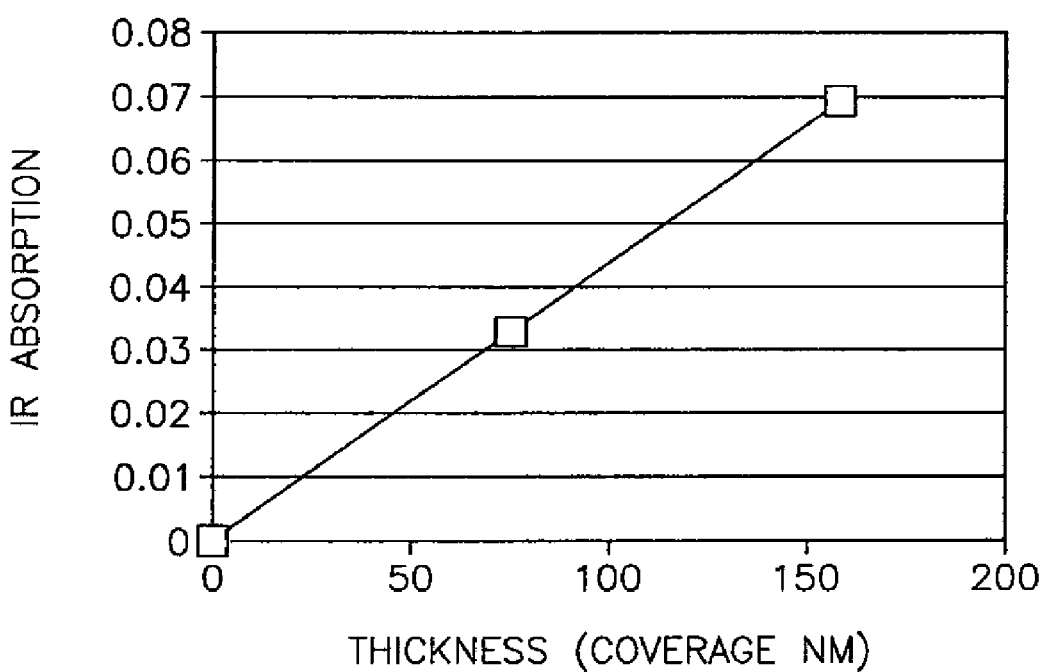
FIG. 11 shows a plot of IR absorbance as a function of $Alq_3$ thickness (coverage).

The IR calibration curves from the data in Table 1 are shown in FIG. 10 (for rubrene) and FIG. 11 (for $Alq_3$). With these calibration curves, absolute coverage of thin films of rubrene, thin films of $Alq_3$, or thin films of rubrene: $Alq_3$ mixtures can be measured. An ellipsometric measurement for a thin film with a nominal ratio of 75:25 (wt:wt) rubrene:$Alq_3$ deposited onto an IR transparent Si substrate was made and the thickness result is shown in Table 2.

determined by first measuring the increase in mass on a quartz crystal balance placed in the deposition chamber in similar depositions to determine a rate of coverage with time, second, measuring the time of deposition of the calibration samples and third, calculating the coverage in nm as the product of rate of coverage×time/$Alq_3$ density. Coverage was determined to be accurate to approximately 5%. Micro-Raman spectra of

TABLE 2

Film thickness data for 75:25 Rubrene:$Alq_3$

Figure 12:
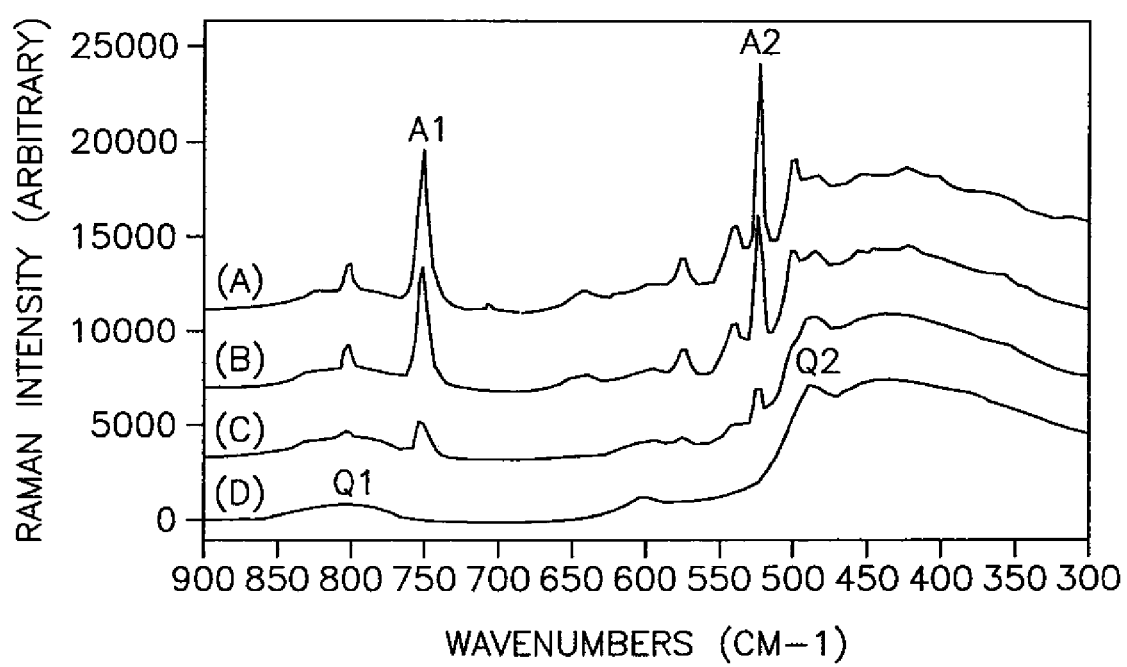
FIG. 12 shows Raman spectra of samples of different thicknesses (coverages) of $Alq_3$ on fused quartz substrates: a) 120 nm, b) 100 nm, c) 30 nm, d) 0 nm (substrate only). Bands of $Alq_3$ used in the calibration for coverage are marked A1 and A2, and those of fused quarts are marked Q1 and Q2.

| | Ellipsometry Thickness | Infrared Absorbance | Calculated Thickness | Total Calculated Thickness | Percent of Layer |
|---|---|---|---|---|---|
| Total Film | 1262 nm | | | 1272 | |
| Rubrene Layer | | 0.0139 | 908 nm | | 71 |
| $Alq_3$ Layer | | 0.0161 | 364 nm | | 29 | the calibration samples were obtained as described in Example 3. FIG. 12 shows the Raman spectra of three calibration samples with different $Alq_3$ coverages and of the fused silica quartz substrate itself. Analytical peaks for $Alq_3$ are marked "A1" and "A2", while those for fused silica quartz are marked "Q1" and "Q2". Because Raman spectroscopy measures scattered light intensity as a function of wavenumber, rather than an absorbance as in the infrared Example 3, calibration of Raman peak intensities (peak heights, peak areas, etc.) in terms of coverage or concentration is made by plotting the relative intensity of the Raman band of interest, divided by the intensity of a Raman band from some reference material. In this example, the heights of the quartz bands marked in FIG. 12 at 796 $cm^{-1}$ and 488 $cm^{-1}$ are used as reference bands. The peak heights of the $Alq_3$ bands at 754 $cm^{-1}$ and 524 $cm^{-1}$ in the calibration samples were divided by those of the two quartz reference bands and are plotted in FIG. 13 vs. $Alq_3$ coverage in nm and best fit straight lines were calculated to generate four calibration curves of relative intensity vs. coverage.

An additional sample on fused quartz, prepared in a different vacuum coater and with a coverage aim of 100 nm $Alq_3$ was subjected to micro-Raman spectroscopic measurement. The relative intensities of $Alq_3$ bands at 754 $cm^{-1}$ and 524 $cm^{-1}$ were calculated relative to the quartz bands at 796 $cm^{-1}$ and 488 $cm^{-1}$. Calculated film thickness was obtained by applying the individual calibration curves of FIG. 13 to the four relative intensities and averaging the values. The resulting average measured $Alq_3$ coverage was 104.6 nm.

In a thin film coating containing a layer of mixed compound X and compound Y, or a multilayer coating containing compound X and compound Y, the relative coverages of X vs. Y can be calibrated in exactly the same way as indicated in this example where $Alq_3$ would be compound X and fused quartz would be compound Y. Bands associated with compounds X and Y would be identified and intensities of those bands would be measured for a series of calibration samples with different coverage ratios of X and Y.

Figure 13:
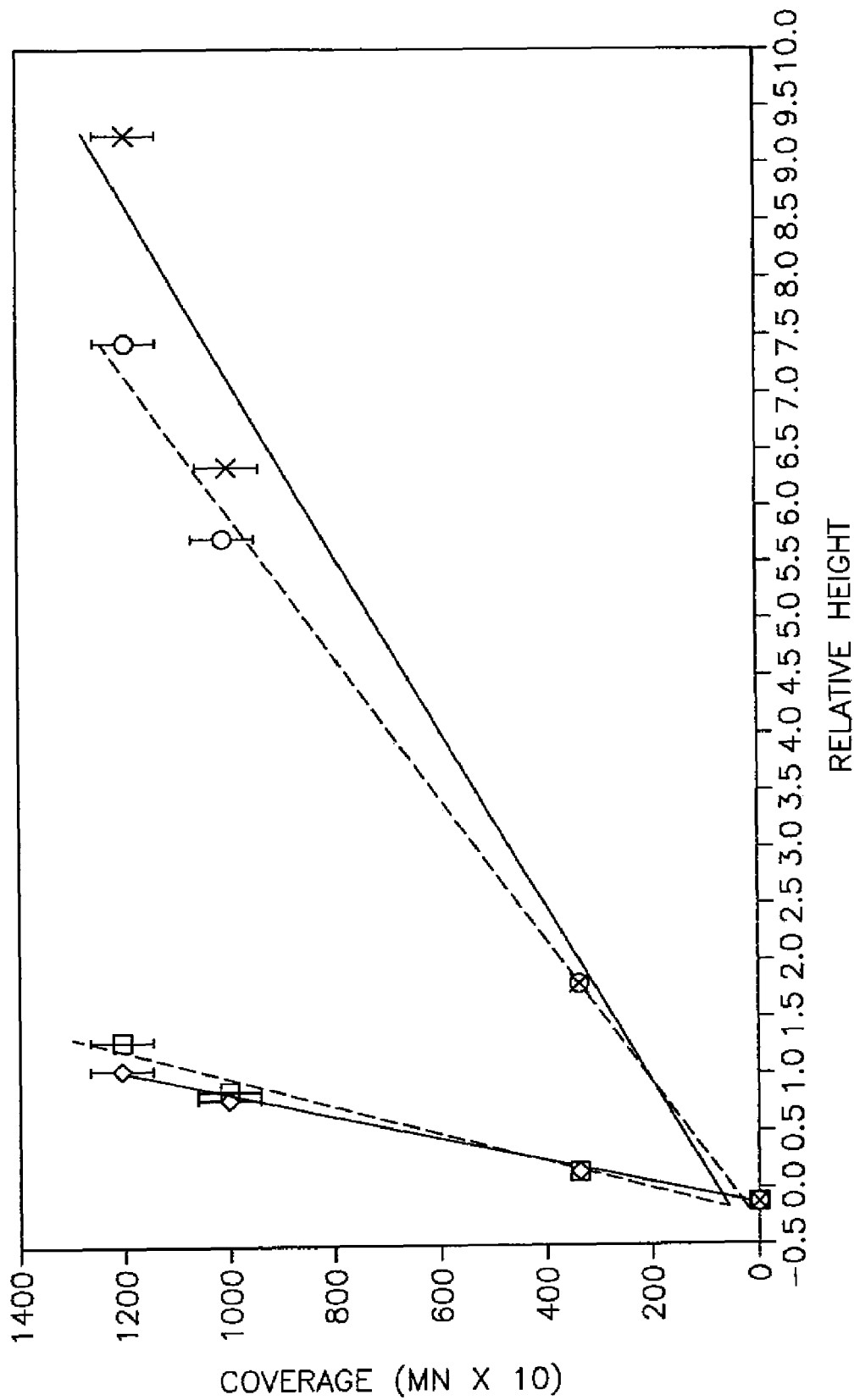
FIG. 13 shows a calibration curve of coverage vs relative peak heights of $Alq_3$ bands vs Quartz bands: Closed Diamonds=A1/Q2, Open Squares=A2/Q2, Closed Circles=A1/Q1, X=A2/Q1.

Relative intensities of X vs. Y would be calculated as shown above for X=$Alq_3$ and Y=fused quartz and plotted as in FIG. 13 vs. the coverage ratio of X/Y. The spectrum of any unknown coated sample of X and Y would then be measured and the coverage ratio of the unknown sample would be calculated from the calibration curve previously obtained.

Example 4 demonstrates that the vibrational spectroscopy technique of Raman is able to determine the relative coverage of organic thin films. Example 4 further demonstrates through this invention that by establishing a reference spectrum library of polymorphs of crystalline powders of an organic material by XRPD, subjecting these reference powders to a vibrational spectroscopy measurement such as Raman spectroscopy to establish a reference spectrum library, and subjecting a thin film of said organic material to a vibrational spectroscopy measurement to obtain a resulting spectrum, a comparison of the resulting spectrum to those spectra in the reference library can be used to determine relative coverages and thicknesses of organic thin films.

Example 5

Invention: Identification of the Phases of Multilayered Organic Thin Films in an Encapsulated Device in the Presence of X-Ray Attenuating Glass A multilayer EL device is comprised of 2 or more organic thin films that are encapsulated to protect the EL device and minimize the effect of ambient air, including oxygen and water, on the decomposition of the organic thin films. Examples 1-4 have demonstrated that XRD is not able to correctly identify polymorphic forms of amorphous thin films. Examples 1-4 have demonstrated that Raman spectroscopy is able to identify polymorphic forms of amorphous thin films using the methods described in this invention. An additional complication in XRD phase identification of thin films in EL devices is that the front of the device encapsulation is comprised of glass. This glass is thick enough that it will attenuate the X-ray beam used in an X-ray diffraction analysis as described in the Experimental section of this invention.

Figure 14:
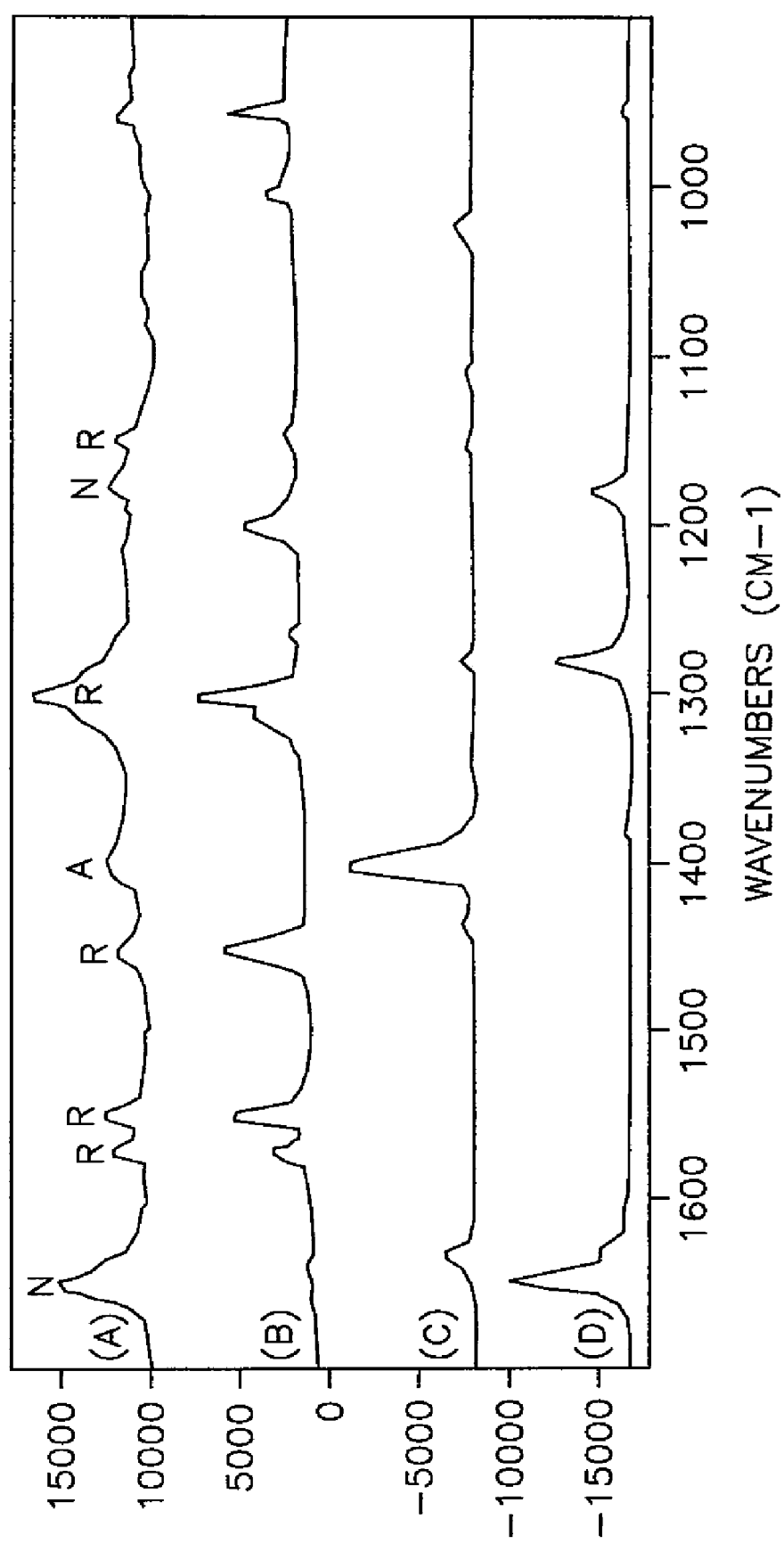
FIG. 14 shows a Raman spectrum of multilayered organic thin films in an encapsulated device in the presence of X-ray attenuating glass, and of reference materials: (a) multilayered device, (b) rubrene powder, (c) α $Alq_3$, and (d) NPB (N,N'-di-1-naphthalenyl-N,N'diphenyl-4,4'-diaminobiphenyl) powder.

A functional EL type device with thin films of Rubrene/$Alq_3$/NPB (NPB Structure 5) deposited on glass and encapsulated with a glass cover was characterized using Raman spectroscopy. FIG. 14 shows the Raman spectrum of this device (a), and also the Raman spectra of rubrene, $Alq_3$ and NPB (b, c and d, respectively) reference materials. Unique bands and shoulders for each of the reference materials are identified in the EL device by letters (R for rubrene, A for $Alq_3$ and N for NPB). $Alq_3$ is identified as the $\alpha$ phase, based on spectra collected for thin films in the reference library.

Example 5 demonstrates that XRPD is not capable of characterizing polymorphic forms of organic thin films if the films are amorphous or encapsulated with an X-ray attenuating medium. Example 5 further demonstrates through this invention that by establishing a reference spectrum library of polymorphs of crystalline powders of an organic material by XRPD, subjecting these reference powders to a vibrational spectroscopy measurement such as Raman spectroscopy to establish a reference spectrum library, and subjecting an amorphous thin film of said organic material to a vibrational spectroscopy measurement to obtain a resulting spectrum, a comparison of the resulting spectrum to those spectra in the reference library can be used to characterize the polymorph of the amorphous material, including amorphous material that is encapsulated in an X-ray attenuating medium.

The invention claimed is:

1. A process for characterizing the phase of an organic material in a thin film comprising:
   establishing a reference spectrum library for potential phases;
   subjecting the film to a vibrational spectroscopy measurement to obtain a resulting spectrum; and
   comparing the resulting spectrum to those in the reference library to characterize the phase of the organic material.

2. The process of claim 1 wherein the reference spectrum library is comprised of the vibrational spectra of potential phases and the corresponding X-ray diffraction characterizations of the potential phases.

3. The process of claim 1 wherein the vibrational spectroscopy measurement includes Raman spectroscopy and infrared spectroscopy.

4. The process of claim 1 wherein the comparison of the measured vibrational spectrum is made numerically, visually, or by use of a computer algorithm.

5. The process of claim 1 in which the thin film is contained in an electronic device.

6. The process of claim 1 in which the thin film has a thickness of 5 nm to 500 nm.

7. The process of claim 1 in which the characterization of the phase is part of a manufacturing process in which such characterization may be part of an automated process or computer algorithm.

8. The process of claim 7 in which the characterization of the phase is part of an automated process or computer algorithm.

9. The process of claim 1 wherein the thin film is a thin film in an electronic device which includes a material that shields the thin film from X-rays.

10. The process of claim 9 in which the thin film has a thickness of 5 nm to 500 nm.

11. A process for identifying a known phase, an undesirable phase or impurity, or of detecting the presence of an unknown phase of an organic material in a thin film, comprising:
   establishing a reference spectrum library for known phases;
   subjecting the film to a vibrational spectroscopy measurement to obtain a resulting spectrum;
   comparing the resulting spectrum to those in the reference library to ascertain the identity of the known phase, the undesirable phase or impurity, or the presence of an unknown phase.

12. The process of claim 11 wherein the thin film is a thin film in an electronic device which includes a material that shields the thin film from X-rays.

13. The process of claim 11 wherein the reference spectrum library is comprised of the vibrational spectra of potential phases and the corresponding X-ray diffraction characterizations of the potential phases.

14. The process of claim 11 wherein the vibrational spectroscopy measurement includes Raman spectroscopy and infrared spectroscopy.

15. The process of claim 11 wherein the comparison of the measured vibrational spectrum is made numerically, visually, or by use of a computer algorithm.

16. The process of claim 11 in which the thin film is characterized while contained within an electronic device.

17. The process of claim 11 in which the characterization of the phase is part of a manufacturing process.

18. The process of claim 11 in which the characterization of the phase is part of an automated process or computer algorithm.

19. A process for characterizing the phase of an organic material in a thin film comprising:
   establishing a reference library containing the X-ray powder diffraction patterns for potential phases;
   subjecting the thin film to an X-ray diffraction measurement to obtain a resulting pattern;
   comparing the resulting pattern to those in the reference library to characterize the phase of the material in the thin film.

20. The process of claim 19 wherein the comparison of the measured X-ray diffraction pattern is made numerically, visually, or by use of a computer algorithm.

21. The process of claim 19 in which the thin film has a thickness of 5 nm to 500 nm.

22. The process of claim 19 in which the characterization of the phase is part of a manufacturing process.

23. The process of claim 22 in which the characterization of the phase is part of an automated process or computer algorithm.

24. A process for determining the relative amounts of two or more phases of an organic material in a thin film comprising:
   establishing for each phase and mixture of phases of interest a quantitative calibration curve relating selected peak heights or peak areas of that phase as determined by vibrational spectroscopy to the amount present;
   subjecting the thin film to a vibrational spectroscopy measurement to obtain a resulting spectrum;
   utilizing the calibration curves for each phase to compare the peak heights or peak areas for phases of interest to calculate the relative amounts of each phase.

25. The process of claim 24 in which the calibration curve is established using infrared or Raman spectroscopy.

26. The process of claim 24 in which phase of the organic material is characterized by X-ray diffraction techniques.

27. The process of claim 24 in which the thin film has a thickness of 5 nm to 500 nm.

28. The process of claim 24 in which the determination of the relative amounts of selected phases is part of a manufacturing process.

29. The process of claim 24 in which the determination of the relative amounts of selected phases is part of an automated process or computer algorithm.

30. A process for determining the absolute amount of the phase of an organic material in a thin film of known thickness or the thickness of a known organic material comprising:
   establishing for that phase a quantitative calibration curve relating selected peak heights or peak areas of that phase as determined by vibrational spectroscopy to the amount present or to the thickness of the known material;
   subjecting the thin film to a vibrational spectroscopy measurement to obtain a resulting spectrum;
   utilizing the calibration curve for the phase of interest to compare the peak heights or peak areas for phase of interest to calculate the absolute amount of that phase for the known film thickness or to calculate the thickness of the known material.

31. The process of claim 30 in which the calibration curve is established using infrared or Raman spectroscopy.

32. The process of claim 30 in which phase of the organic material is characterized by X-ray diffraction techniques.

33. The process of claim 30 in which the thin film has a thickness of 5 nm to 500 nm.

34. The process of claim 30 in which the determination of the absolute amount of a selected phase is part of a manufacturing process.

35. The process of claim 30 in which the determination of the absolute amount of a selected phase is part of an automated process or computer algorithm.

* * * * *